United States Patent
Hashizume et al.

(10) Patent No.: US 12,338,198 B2
(45) Date of Patent: Jun. 24, 2025

(54) CANCER CELL GROWTH INHIBITING COMPOSITION AND PROCESSED FOOD

(71) Applicants: HAGIHARA FARM PRODUCTION INSTITUTE CO., LTD., Nara (JP); KINKI UNIVERSITY, Osaka (JP); MIE UNIVERSITY, Mie (JP)

(72) Inventors: Toshiharu Hashizume, Nara (JP); Takashi Kitayama, Nara (JP); Gengo Kashiwazaki, Nara (JP); Satoru Hirabayashi, Nara (JP); Yoshimi Utaka, Nara (JP); Keigo Taneda, Nara (JP); Tomohiro Itoh, Mie (JP)

(73) Assignees: HAGIHARA FARM PRODUCTION INSTITUTE CO., LTD., Nara (JP); KINKI UNIVERSITY, Osaka (JP); MIE UNIVERSITY, Mie (JP)

( * ) Notice: Subject to any disclaimer, the term of this patent is extended or adjusted under 35 U.S.C. 154(b) by 875 days.

(21) Appl. No.: 17/431,341

(22) PCT Filed: Feb. 21, 2020

(86) PCT No.: PCT/JP2020/007102
§ 371 (c)(1),
(2) Date: Aug. 16, 2021

(87) PCT Pub. No.: WO2020/171210
PCT Pub. Date: Aug. 27, 2020

(65) Prior Publication Data
US 2022/0135514 A1 May 5, 2022

(30) Foreign Application Priority Data
Feb. 21, 2019 (JP) .................................. 2019-029800

(51) Int. Cl.
*C07C 233/09* (2006.01)
*A23L 33/175* (2016.01)
(Continued)

(52) U.S. Cl.
CPC .......... *C07C 233/09* (2013.01); *A23L 33/175* (2016.08); *A61P 35/00* (2018.01);
(Continued)

(58) Field of Classification Search
CPC ................ C07C 233/05; C07C 233/09; C07C 211/21; A61P 35/00; A23V 2002/00
See application file for complete search history.

(56) References Cited

U.S. PATENT DOCUMENTS

| 4,456,603 | A | * | 6/1984 | Yamatsu | ................. C07C 51/08 514/315 |
| 4,959,370 | A |   | 9/1990 | Crews et al. | |

(Continued)

FOREIGN PATENT DOCUMENTS

| CN | 108601756 A | 9/2018 |
| EP | 1069130 | 1/2001 |

(Continued)

OTHER PUBLICATIONS

International Search Report issued in International Patent Application No. PCT/JP2020/007102, dated Mar. 31, 2020, along with an English translation thereof.
(Continued)

*Primary Examiner* — Yate' K Cutliff
(74) *Attorney, Agent, or Firm* — GREENBLUM & BERNSTEIN P.L.C.

(57) ABSTRACT

Phytol contained in watermelon sprouts is known to have a cancer cell growth inhibiting effect. However, there is a problem that an amount of phytol to be taken for exhibiting cancer cell growth inhibition is large.

(Continued)

A cancer cell growth inhibiting composition comprising at least one of compounds having a structure represented by Formula (1), Formula (2), Formula (6), Formula (7) or Formula (8), or a pharmaceutically acceptable salt thereof as main components has a higher cancer cell growth inhibiting effect than phytol.

[Chemical 100]

(1)

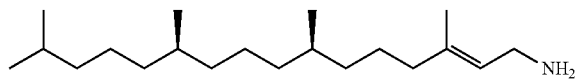

[Chemical 101]

(2)

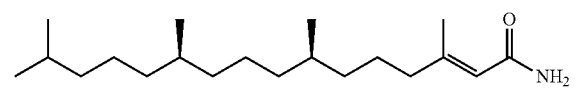

[Chemical 102]

(6)

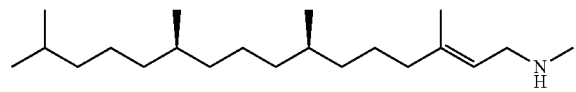

[Chemical 103]

(7)

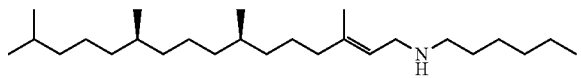

[Chemical 104]

-continued (8)

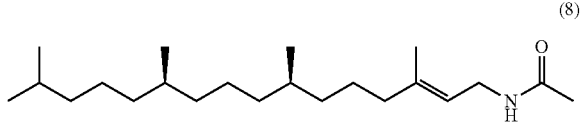

8 Claims, 6 Drawing Sheets

(51) Int. Cl.
    *A61P 35/00*     (2006.01)
    *C07C 211/21*    (2006.01)
    *C07C 233/05*    (2006.01)

(52) U.S. Cl.
    CPC .......... *C07C 211/21* (2013.01); *C07C 233/05*
    (2013.01); *A23V 2002/00* (2013.01)

(56) References Cited

U.S. PATENT DOCUMENTS

2005/0158329 A1* 7/2005 Ghosh ................ A61K 31/045
                                                        514/724
2019/0343909 A1   11/2019 Itoh et al.

FOREIGN PATENT DOCUMENTS

EP         1069130 A1 * 1/2001  ............. C07H 13/12
JP         56-32442       4/1981
WO         2017/131175    8/2017

OTHER PUBLICATIONS

Office Action issued in CN Patent Application No. 202080015568.4, May 29, 2024, (includes X/Y/A chart as statement of relevance).

* cited by examiner

CANCER CELL GROWTH INHIBITING COMPOSITION AND PROCESSED FOOD

TECHNICAL FIELD

The present invention relates to a pharmaceutical composition and a processed food having a cancer cell growth inhibiting effect having a phytol-based material.

BACKGROUND ART

It is known that extracts of watermelon sprouts have cancer cell growth inhibiting effect (Patent Literature 1). In this literature, it has been shown that out of the extracts, phytol and lutein are particularly effective to exert the effect. Since these substances have no effect on normal cells, it is expected that they can provide anticancer medical compositions with fewer side effects.

CITATION LIST

Patent Literature

Patent Literature 1: International Publication No. 2017/131175

SUMMARY OF INVENTION

Technical Problem

Phytol and lutein have been expected to be used as anticancer medical compositions. However, there is a problem that an amount needed is large in order to exert an effect.

Solution to Problem

In view of the above problems, it is an object of the present invention to provide a material having a high cancer cell growth inhibiting effect.

More specifically, cancer cell growth inhibiting composition according to the present invention is characterized in that at least one of a compound having a structure represented by Formula (1), Formula (2), Formula (6), Formula (7) or Formula (8), or a pharmaceutically acceptable salt thereof is a main component.

[Chemical 1]

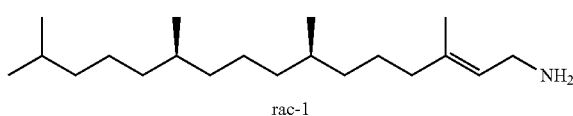

rac-1 (1)

[Chemical 2]

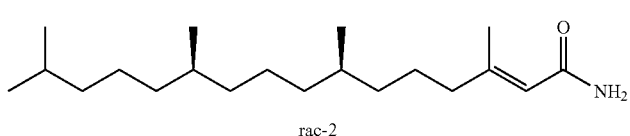

rac-2 (2)

[Chemical 3]

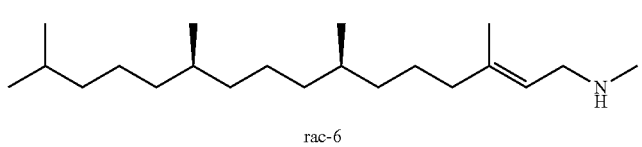

rac-6 (6)

[Chemical 4]

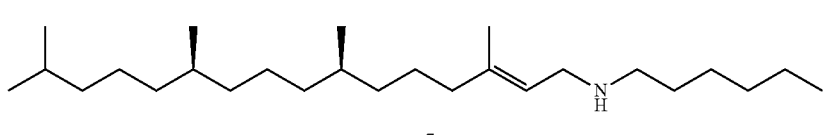

rac-7 (7)

[Chemical 5]

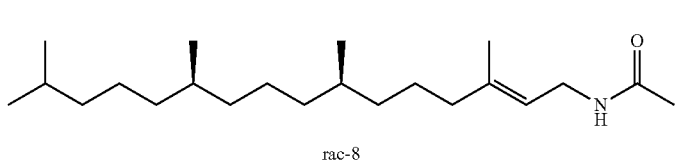

rac-8 (8)

Note that "rac-1," "rac-2," "rac-6," "rac-7," and "rac-8" in Formula (1), Formula (2), Formula (6), Formula (7) and Formula (8) are tentative names of respective compounds in this description, and are not included in structures of the respective compounds themselves.

Also, the present invention can be provided as a processed food. More specifically, a processed food according to the present invention is characterized in that it has a compound having a structure represented by Formula (1), Formula (2), Formula (6), Formula (7) or Formula (8), or a pharmaceutically acceptable salt thereof. In addition, a compound having a structure of Formula (1), Formula (2), Formula (6), Formula (7) or Formula (8) has been synthesized for the first time and is also a novel substance.

Advantageous Effects of Invention

The cancer cell growth inhibiting composition according to the present invention can inhibit the growth of cancer cells. Therefore, it can be suitably utilized as a pharmaceutical composition for anti-cancer. As the processed foods according to the present invention also contain compounds with inhibitory effects on cancer cell growth, regularly taking the processed foods in forms of supplements can lead to prevention of cancer.

DESCRIPTION OF EMBODIMENTS

Figure 1:
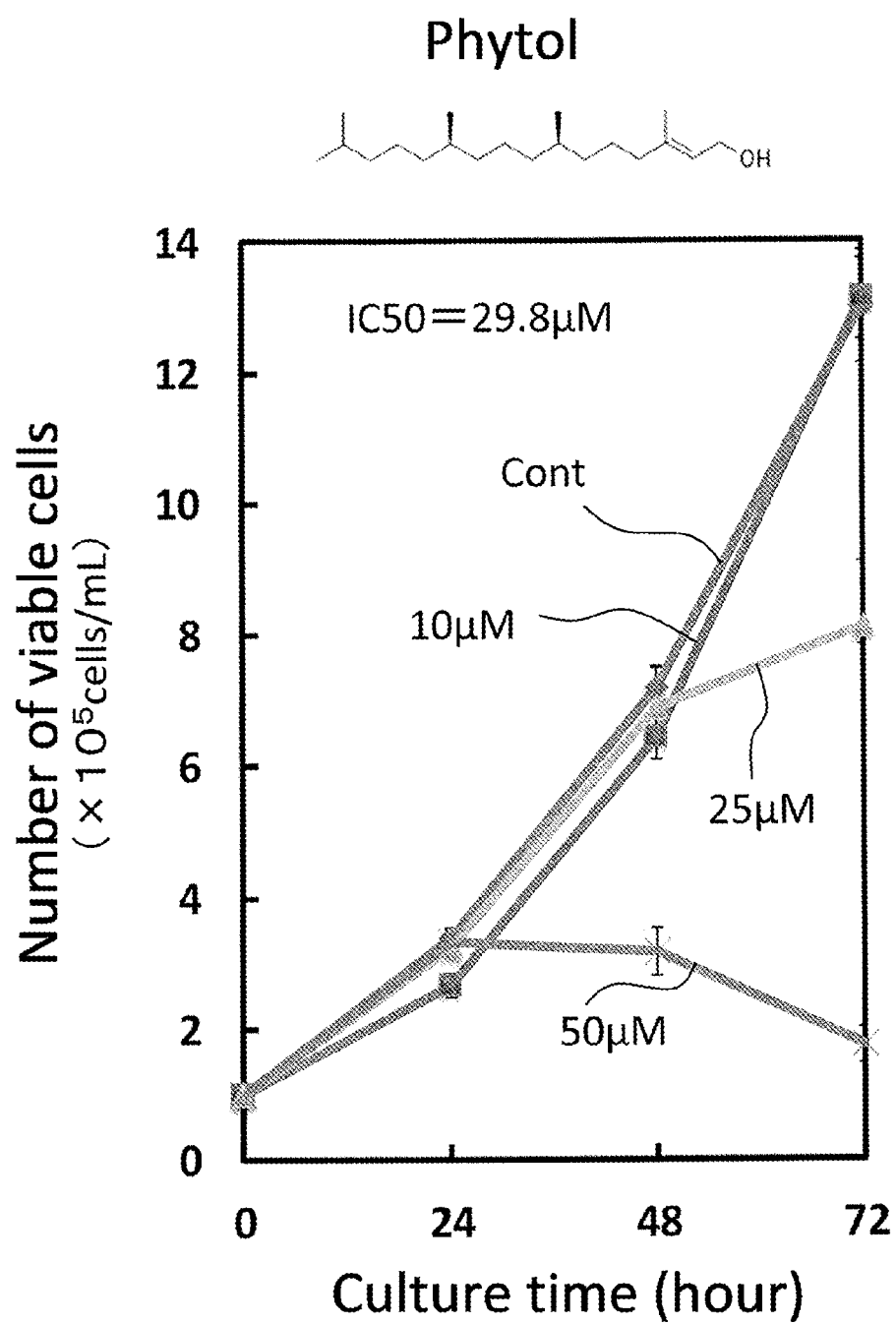
FIG. 1 is a graph showing cancer cell growth inhibiting effect of phytol.

Hereinafter, the present invention will be described by way of drawings and examples. Note that the following description exemplifies an embodiment and an Example of the present invention and the present invention is not limited to the following description. The following description may be changed or modified within a scope not departing from the gist of the present invention.

The cancer cell growth inhibiting composition according to the present invention is composed of a compound having a structure represented by Formula (1), Formula (2), Formula (6), Formula (7) or Formula (8), or a pharmaceutically acceptable salt thereof.

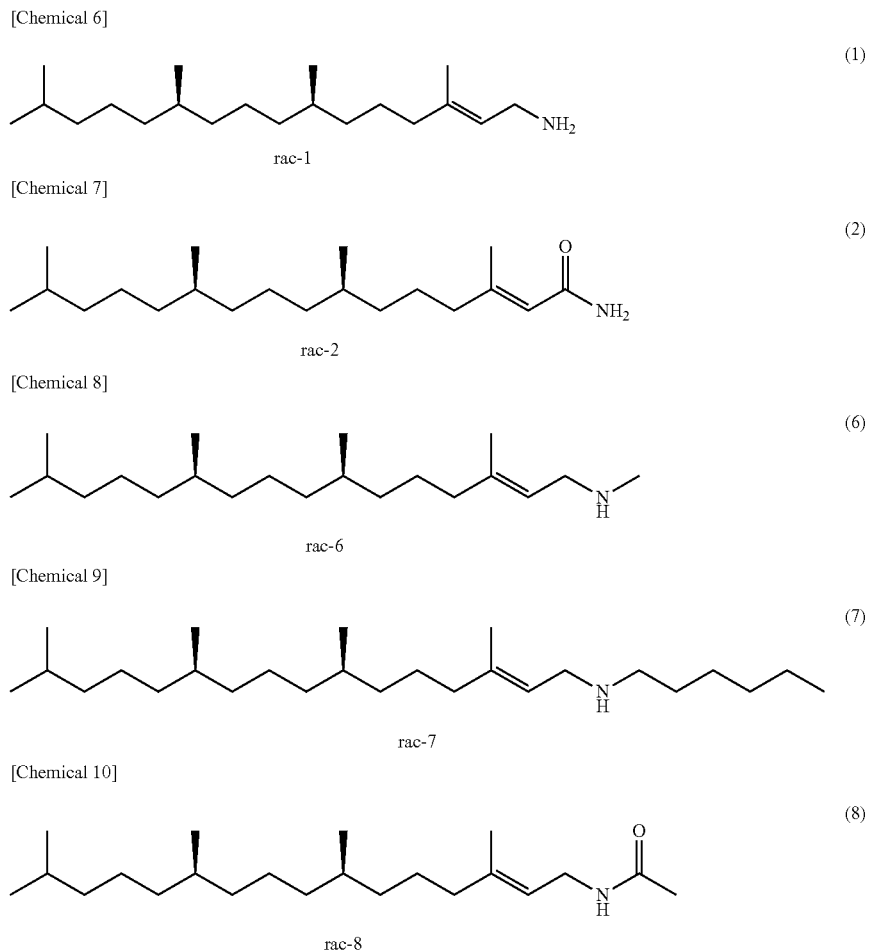

The compound (rac-1) of Formula (1) is (E)-3,7,11,15-tetramethylhexadec-2-en-1-amine ((E)-3,7,11,15-tetramethylhexadeca-2-en-1-amine. Hereinafter, referred to as "aminophytol."), and the compound (rac-2) of Formula (2) is (E)-3,7,11,15-tetramethylhexadec-2-enamide ((E)-3,7,11,15-tetramethylhexadeca-2-enamide. Hereinafter, referred to as "amidophytol.").

The compound (rac-6) of Formula (6) is (E)-pentamethylhexadec-2-en-1-amine ((E)-N,3,7,11,15-pentamethylhexadeca-2-en-1-amine. Hereinafter, referred to as "methylaminophytol" or "monomethylaminophytol."), and the compound (rac-7) of Formula (7) is (E)-N-hexyl-3,7,11,15-tetramethylhexadec-2-en-1-amine ((E)-N-hexyl-3,7,11,15-tetramethylhexadeca-2-en-1-amine. Hereinafter, referred to as "hexylaminophytol" or "monohexylaminophytol." and the compound (rac-8) of Formula (8) is (E)-N-(3,7,11,15-tetramethylhexadec-2-en-1-yl) acetamide ((E)-N-(3,7,11,15-tetramethylhexadeca-2-en-1-yl) acetamido. Hereinafter, it is referred to as "acetamidophytol.").

When these compounds are utilized as cancer cell growth inhibiting composition (pharmaceutical compositions), the compounds may be mixed with pharmaceutically acceptable acids to be utilized as salts in solvents such as water, methanol, ethanol, acetone, and the like for example, in addition to being utilized alone. Herein, pharmaceutically acceptable acids include inorganic acids such as hydrochloric acid, hydrobromide, sulfate, phosphate, nitric acid, or organic acids such as acetic acid, propionic acid, oxalic acid, succinic acid, lactic acid, malate, tartrate, citric acid, maleic acid, fumarate, methanesulfonic acid, p-toluenesulfonic acid, ascorbic acid, etc.

The dosage form of the pharmaceutical composition according to the present invention is not particularly limited, and may be either oral or parenteral dosage form. In addition, depending on the dosage form, a suitable preparation form can be employed. For example, the pharmaceutical composition according to the present invention may be prepared in a form of an injection, or in various preparations such as an oral preparation like a capsule, a tablet, a granule, a powder, a pill, a fine granule, etc., a rectal administration, an oil-and-fat suppository, or an aqueous suppository.

Further, the cancer cell growth inhibiting composition according to the present invention can be also provided as processed foods. The processed foods include not only general processed foods including foods of taste or health foods such as candy, gum, jelly, biscuit, cookie, rice cracker, bread, noodles, fish and livestock meat paste products, tea, soft drinks, coffee beverages, milk beverages, whey beverages, lactic acid bacteria beverages, yogurt, ice cream, pudding or the like for example but also health-promoting foods such as specified health foods, nutritional function foods or the like specified in the Health and Functional Foods System of the Ministry of Health, Labour and Welfare, and further include dietary supplements, feed, food additives, etc.

By adding cancer cell growth inhibiting composition into raw materials of the processed foods, the processed foods according to the present invention can be prepared.

EXAMPLE

<1. Compound Synthesis>
Aminophytol and amidophytol synthesized example is shown below.
<1-1>

(E)-Synthesis of (E)-1-Bromo-3,7,11,15-tetramethylhexadec-2-ene: (E)-1-bromo-3,7,11,15-tetramethylhexadeca-2-ene (rac-3)

[Chemical 11]

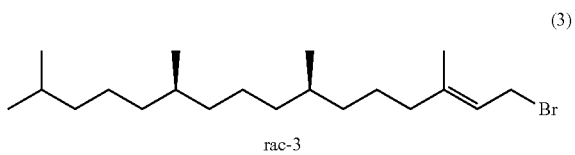

rac-3

First, a compound of Formula (3) was synthesized. The "rac-3" is a tentative number of a compound of a structure of Formula (3) in the present description and is not included in a structure of the compound of Formula (3).

$Et_2O$ (5 mL) was added to a 100-mL two-mouth flask, phytol (500 mg, 1.686 mmol) dissolved in $Et_2O$ (20 mL) was added and stirred at 0° C. for a while. Subsequently, phosphorus tribromide (0.064 mL, 0.674 mmol, 0.4 eq) was instilled and stirred at the same temperature for 30 minutes.

Reaction was confirmed by TLC (Thin-Layer Chromatography: thin layer chromatography) (Hexane (hexane)/AcOEt (ethyl acetate)=5/1). After confirming that the raw material had disappeared on the TLC, reaction was stopped by dropping a saturated aqueous sodium bicarbonate solution, extraction was made with ethyl acetate, and an organic layer was collected and neutralized with a saturated aqueous sodium bicarbonate solution, washed with brine, dried over anhydrous sodium sulfate, and sodium sulfate was removed by natural filtration, and the solution was concentrated under reduced pressure on a rotary evaporator to obtain 449.9 mg of a crude product in a reddish brown oil state. No purification procedure was performed.

Yield (74%: reddish brown oil) $^1H$ NMR (CDCl3, 400 MHz): δ 0.82-0.89 (m, 14H), 1.02-1.41 (m, 21H), 1.50-1.62 (m, 2H), 1.72 (d, 3H, J=1.3 Hz), 2.02 (t, 2H, J=7.6 Hz), 4.04 (d, 2H, J=8.4 Hz), 5.53 (t, 1H, J=8.4 Hz)
<1-2>

Synthesis of (E)-(3,7,11,15-tetramethylhexadec-2-en-1-yl)isoindoline-1,3-dione: (E)-(3,7,11,15-tetramethylhexadeca-2-en-1-yl) isoindolin-1,3-dione (rac-4)

[Chemical 12]

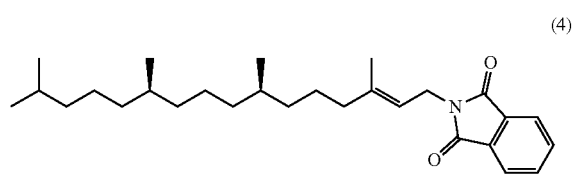

rac-4

Next, a compound of Formula (4) was synthesized using rac-3 as a raw material.

The "rac-4" is a tentative number of a compound of a structure of Formula (4) in the present description and is not included in a structure of the compound of Formula (4).

The rac-3 (449.9 mg, 1.252 mmol) dissolved in DMF (7 mL) under a nitrogen atmosphere was added to a 100 mL 3 neck flask, and stirred at room temperature for a while. Thereafter, potassium phthalimide salt (301.4 mg, 1.627 mmol, 1.3 eq) dissolved in DMF (5 mL) was added and stirred at the same temperature for 2 hours.

Reaction was confirmed by TLC (Hexane only). After confirming that the raw material had disappeared on the TLC, reaction was stopped by dropping $H_2O$ at the same temperature and extraction was made with ethyl acetate. An organic layer was collected and neutralized with saturated aqueous sodium bicarbonate. After washing with brine, it was dried over anhydrous sodium sulfate, and sodium sulfate was removed by natural filtration. Solution was concentrated in vacuo on a rotary evaporator to give 591.5 mg of a crude yellow crystalline product.

This crude product was purified by open column chromatography (Hexane/AcOEt=20/1) to give a yellow oily product in a yield of 422.3 mg.

Yield (79%: yellow oil) $^1$H NMR (CDCl$_3$, 400 MHz): δ 0.80-0.88 (m, 12H), 0.99-1.57 (m, 19H), 1.82 (s, 3H), 1.95 (t, J=7.5 Hz), 4.28 (d, 2H, J=7.3 Hz), 5.26 (tq, 1H, J=7.3, 1.2 Hz), 7.81-7.86 (m, 2H), 7.67-7.72 (m, 2H).

<1-3> Synthesis of Aminophytol

Synthesis of (E)-3,7,11,15-tetramethylhexadec-2-en-1-amine: (E)-3,7,11,15-tetramethylhexadeca-2-en-1-amine (aminophytol (rac-1))

(E)-3,7,11,15-tetramethylhexadec-2-en-1-amine: (E)-3,7, 11,15-tetramethylhexadeca-2-en-1-amine Aminophytol (rac-1) was synthesized using the above rac-4 as a raw material. Rac-4 (300 mg, 0.705 mmol) dissolved in ethanol (10 mL) under a nitrogen atmosphere was added to a 100 mL 3 necked flask, and hydrazine monohydrate (0.103 mL, 2.114 mmol, 3.0 eq) was added dropwise and stirred at room temperature for 2 hours. Reaction was confirmed by TLC (Hexane/AcOEt=20/1).

After confirming that the raw material had disappeared on the TLC, suction filtration was performed, and filtrate was collected and extraction was made with ethyl acetate, and an organic layer was collected and washed with brine, and then dried over anhydrous sodium sulfate, and sodium sulfate was removed by natural filtration, and solution was concentrated in vacuo on a rotary evaporator under reduced pressure to obtain 246.9 mg of a crude product of yellow crystals. The crude product was purified by open column chromatography (MeOH (methanol)/$CH_2Cl_2$ (dichloromethane)=95/5, containing 1% 1M ammonia-water) and the yellow oil-like product (aminophytol) was obtained at 64.5 mg (31%) yield.

Yield (31%: yellow oil) $^1$H NMR (CDCl$_3$, 400 MHz): δ 0.80-0.91 (m, 12H), 1.02-1.55 (m, 21H), 1.61 (s, 3H), 1.96 (t, 2H, J=7.9 Hz), 3.28 (d, 2H, J=6.9 Hz), 5.25 (tq, 1H, J=6.9, 1.3 Hz).

<1-4> Synthesis of Amidophytol

Synthesis of (E)-3,7,11,15-tetramethylhexadec-2-enamide:(E)-3,7,11,15-tetramethylhexadeca-2-enamide (amidophytol (rac-2))

Amidophytol was synthesized from phytanic acid after phytanic acid (CAS No. 14721-66-5) was synthesized.

First, phytanic acid (rac-5) of the formula (5) was synthesized. The "rac-5" is a tentative number in the present description of phytanic acid of a structure of Formula (5) and is not included in a structure of the compound of Formula (5).

[Chemical 13]

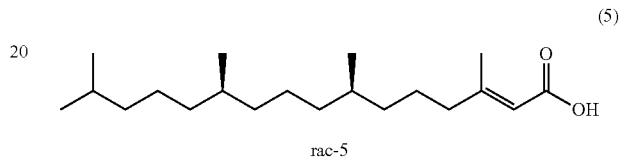

(5)

rac-5

A mixture of acetonitrile (0.150 mL) and water (0.150 mL) was added to a 10-mL two-mouth flask, iodobenzene diacetate (477.9 mg, 1.484 mmol, 2.2 eq) and a catalytic dose of TEMPO (21.1 mg, 0.135 mmol were added, and the mixture was stirred at room temperature under $N_2$ atmosphere for some time. Subsequently, phytol (200 mg, 0.674 mmol) dissolved in mixed solution of acetonitrile (0.750 mL) and water (0.750 mL) was added dropwise at the same temperature under $N_2$ atmosphere, and stirred at room temperature under $N_2$ atmosphere for 14 hours.

Reaction was confirmed by TLC (Hexane/AcOEt=5/1). Although a raw material remained on the TLC, progress of the reaction could not be confirmed, so that extraction was made with ethyl acetate, an organic layer was collected and washed with brine, and then dried over anhydrous sodium sulfate, and the solution was removed by natural filtration and concentrated under reduced pressure on a rotary evaporator to obtain 308.6 mg of a crude product in a red oil state. This crude product was purified by open column chromatography (Hexane/AcOEt=15/1) to obtain a yellow oily product in a yield of 47.5 mg (23%), but was further purified by preparative HPLC due to insufficient purity to obtain a yellow oily phytanic acid (rac-5) in a yield of 21.8 mg (yield: 10%)

Yield (23%: yellow oil) $^1$H NMR (CDCl$_3$, 400 MHz): δ 0.80-0.88 (m, 12H), 1.05-1.53 (m, 19H), 2.07-2.025 (m, 5H), 5.69 (bs, 1H). $^{13}$C NMR (CDCl$_3$, 100 MHz): δ 19.1, 19.7, 19.8, 22.6. 22.7, 24.5, 24.8, 24.9, 28.0, 32.6, 32.8, 36.5, 37.3, 37.4, 39.4, 41.5, 115.0, 153.1, 163.6.

Phytanoic acid (rac-5) (96.8 mg, 0, 312 mmol) dissolved in THF (1.0 mL) was added to a 5-mL screw tube, 28% aqueous ammonia solution (0.200 mL, 2.959 mmol, 9.5 eq) was added dropwise, and was stirred at room temperature for a while. Subsequently, DMT-MM (4-(4,6-Dimethoxy-1,3,5- triazin-2-yl)-4-methylmorpholinium Chloride n-Hydrate: 129.4 m g, 0.468 mmol, 1.5 eq) was added as a condensing agent and stirred at room temperature for 16 hours. Reaction was confirmed by TLC (Hexane/AcOEt=3/1).

Although a raw material remained on the TLC, since progress of the reaction was not confirmed, extraction was made with ethyl acetate, washing was made with brine, drying was made over anhydrous sodium sulfate, and sodium sulfate was removed by natural filtration, and solution was concentrated under reduced pressure on a rotary evaporator to obtain 104.5 mg of a white crystalline crude product. This crude product was purified by open column chromatography (Hexane/AcOEt=1/1), and a white crystalline product was obtained in a yield of 14.1 mg (15%), but since purity was insufficient, purification was made further by preparative HPLC to obtain a product of white crystals (amidophytol) in a yield of 7.2 mg (yield: 8%).

Yield (15%: white solid) $^1$H NMR (CDCl$_3$, 400 MHz): δ 0.80-0.91 (m, 12H), 1.02-1.56 (m, 19H), 2.09 (td, 2H, J=7.7, 2.2 Hz), 2.15 (d, 3H, J=1.0 Hz), 5.31 (br s, 2H), 5.61 (d, 1H, J=1.2 Hz). HRMS m/z [M+Na]$^+$ Calcd for C$_{20}$H$_{39}$NaNO$^+$ 377.2929. Found 377.2929.

169.1 mg of yellow oil-like crude product. This crude product was purified by open column chromatography (Hexane/AcOEt=1/1) to give a yellow oily product in a yield of 77.8 mg. Due to insufficient purity, again, the product was purified by open column chromatography (MeOH/AcOEt=1/1, triethylamine 1%) to give a yellow oily product in 28.5 mg (15%) yield. Thereafter, the product was purified again by open column chromatography (MeOH/AcOEt=1/5, triethylamine 1%) to obtain a yellow oil-like product in a yield of 17.8 mg (9%)

Yield (9%: Yellow solid). $^1$H NMR (CDCl$_3$, 500 MHz): δ 5.24 (1H, td, J=13.5, 1.4 Hz), 3.19 (2H, d, J=6.9 Hz), 2.42 (2H, s), 2.01-1.88 (3H, m), 1.63 (3H, s), 1.57-1.48 (1H, m), 1.46-1.16 (13H, m), 1.16-0.99 (7H, m), 0.89-0.80 (12H, m). $^{13}$C NMR (CDCl$_3$, 100 MHz): δ 137.42, 120.95, 47.8, 38.7, 38.1, 36.2, 36.2, 36.1, 35.4, 34.6, 31.6, 31.5, 26.8, 24.0, 23.6, 23.3, 21.5, 21.4, 18.6, 15.0. HRMS m/z [M+H]$^+$ Calcd for C$_{21}$H$_{44}$N$^+$ 310.3468. Found 310.3477.

<1-6> Synthesis of Hexylaminophytol

Synthesis of (E)-N-hexyl-3,7,11,15-tetramethyl-hexadec-2-en-1-amine:(E)-N-hexyl-3,7,11,15-tetramethylhexadeca-2-en-1-amine (rac-7)

[Chemical 15]

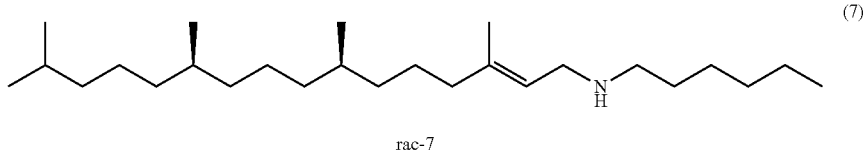

rac-7

<1-5> Synthesis of Methylaminophytol

Synthesis of (E)-N,3,7,11,15-pentamethylhexadec-2-en-1-amine:(E)-N,3,7,11,15-pentamethylhexadeca-2-en-1-amine (rac-6)

[Chemical 14]

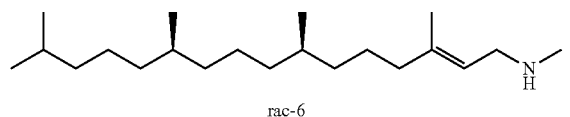

rac-6

40% Methylamine (0.740 mL, 21.0 mmol, 33.4 eq) dissolved in CH$_2$Cl$_2$ (4.0 mL) was added to a 20-mL screw tube and stirred at room temperature. Subsequently, rac-3 (225.0 mg, 0.630 mmol) dissolved in CH$_2$Cl$_2$ (4.0 mL) was added dropwise over 10 minutes and stirred at room temperature for 1 hour. Reaction was confirmed by TLC (Hexane/AcOEt=5/1).

After confirming disappearance of a raw material on the TLC, water was added dropwise for dilution, extraction was made with CH$_2$Cl$_2$, washing was made with Brine, drying was made with anhydrous sodium sulfate, and sodium sulfate was removed by natural filtration, and solution was concentrated in vacuo with a rotary evaporator to obtain N-hexylamine (4.20 mL, 3.20 g, 31.7 mmol, 33.4 eq) dissolved in CH$_2$Cl$_2$ (5 mL) was added to a 50-mL screw tube and stirred at room temperature. Subsequently, rac-3 (342.7 mg, 0.950 mmol) dissolved in CH$_2$Cl$_2$ (5 mL) was added dropwise over 10 minutes and stirred at room temperature for 2 hours. Reaction was confirmed by TLC (Hexane/AcOEt=5/1).

After confirming disappearance of the raw materials on the TLC, water was added dropwise for dilution, extraction was made with CH$_2$Cl$_2$, washing was made with Brine, drying was made with anhydrous sodium sulfate, sodium sulfate was removed by natural filtration, water was added to the solution, reagent residue was removed with a rotary evaporator, and 352.5 mg of yellow oil-like crude product was obtained. This crude product was purified by open column chromatography (Hexane/AcOEt=10/1 and AcOEt (triethylamine 1%)) to give a yellow oily product in a yield of 270.2 mg.

Yield (75%: Yellow solid). $^1$H NMR (CDCl$_3$, 500 MHz): δ 5.25 (1H, td, J=13.9, 1.3 Hz), 3.21 (2H, d, J=3.2 Hz), 2.59 (2H, t, J=2.5 Hz), 2.01-1.90 (2H, m), 1.62 (3H, s), 1.57-1.44 (3H, m), 1.44-1.17 (19H, m), 1.17-1.00 (7H, m), 0.91-0.81 (15H, m). $^{13}$C NMR (CDCl$_3$, 125 MHz): δ 137.8, 122.7, 49.6, 47.3, 39.9, 39.3, 37.4, 37.3, 37.2, 36.6, 32.7, 32.6, 31.8, 30.1, 27.9, 27.1, 25.1, 24.7, 24.4, 22.7, 22.6, 19.7, 16.1, 14.0. HRMS m/z [M+Na]$^+$ Calcd for C$_{26}$H$_{51}$NaNO$^+$ 402.4070. Found 402.4076.

<1-7> Synthesis of Acetamidophytol.

Synthesis of (E)-N-(3,7,11,15-tetramethylhexadec-2-en-1-yl)acetamide:(E)-N-(3,7,11,15-tetramethylhexadeca-2-en-1-yl)acetamide (rac-8)

[Chemical 16]

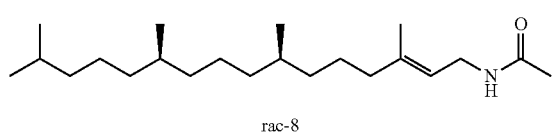

(8)

rac-8

Rac-1 (100-mg, 0.340 mmol) and triethylamine (0.15 mL, 1.1 mmol, 3.1 eq) dissolved in dry THF (1.0 mL) were added to a 5-mL screw tube and stirred at 0° C. under $N_2$ atmosphere. Subsequently, acetyl chloride (0.040 mL, 0.53 mmol, 1.5 eq) dissolved in dry THF (1.0 mL) was added dropwise and stirred at the same temperature under $N_2$ atmosphere for 2 hours. The reaction was confirmed by TLC (Hexane/AcOEt=1/1).

After confirming disappearance of a raw material on the TLC, water was added dropwise to stop the reaction, extraction was made with ethyl acetate, and the organic layer was collected and washed with water, and then dried over anhydrous sodium sulfate, and sodium sulfate was removed by natural filtration, and the solution was concentrated in vacuo on a rotary evaporator under reduced pressure to obtain 103.1 mg of a yellow oil-like crude product. This crude product was purified by open column chromatography (Hexane/AcOEt=2/1) to give a yellow oily product in 68.5 mg (60%) yield.

Yield (60%: Yellow solid) $^1$H NMR (CDCl$_3$, 400 MHz): δ 5.35 (1H, br s), 5.18 (1H, td, J=14.0, 1.4 Hz), 3.84 (2H, t, J=12.2 Hz), 1.97 (5H, s), 1.65 (4H, s), 1.56-1.47 (1H, m), 1.46-1.18 (1H, m), 1.16-1.00 (7H, m), 0.88-0.82 (13H, m). $^{13}$C NMR (CDCl$_3$, 100 MHz): δ 169.8, 140.6, 119.5, 39.8, 39.4, 37.6, 37.4, 37.3, 37.2, 36.7, 32.8, 32.7, 28.0, 25.2, 24.8, 24.5, 23.3, 22.7, 22.6, 19.8, 19.7, 16.2. HRMS m/z [M+Na]$^+$ Calcd for $C_{22}H_{43}NaNO^+$ 360.3237. Found 360.3235.

<2. Cell Culture>

Human leukemic T-cell line Jurkat cells were obtained from the RIKEN BioResource Research Center (Tsukuba-shi, Ibaraki Prefecture). The cells were cultured in RPMI1640 medium (Wako Pure Chemical Industries, Ltd., Osaka-shi, Osaka Prefecture) containing 10% fetal bovine serum (Thermo Fisher Scientifics, K.K., MA, USA), 100 U/mL penicillin and 100 μg/mL spletomycin (both Life Technologies, Carlsbad, CA, USA) at 37° C. in a 95% air-5% CO2 environment.

<3. Effect of Compounds on Growth of Human Leukemic T-Cell Line Jurkat Cells>

Jurkat cells were adjusted to 1×10$^5$ cells/mL and seeded in 24-well multi-plates (Thermo Fisher Scientifics K. K.) by 500 μL/well. After seeding, phytol, aminophytol, amidophytol, methylaminophytol, hexylaminophytol, and acetamidophytol were adjusted with distilled water to a final concentration of 10 μM, 25 μM, and 50 μM respectively, and then added. Note that no compound is added to a control. After adding respective compounds, the cells were stained with Tripan Blue (Life Technologies) after 24, 48, and 72 hours, and live cells were counted using a hemocytometer.

Figure 2:
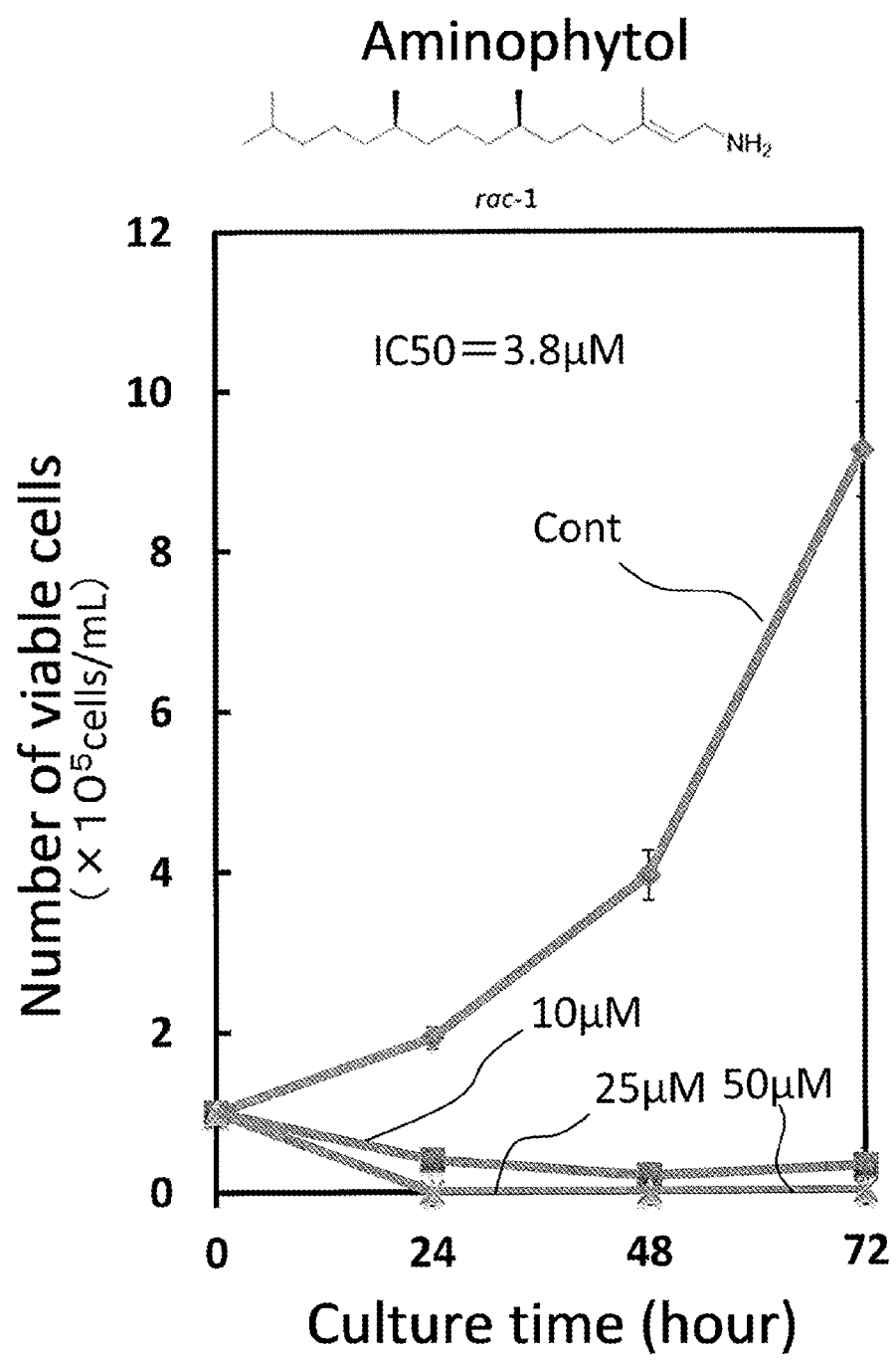
FIG. 2 is a graph showing cancer cell growth inhibiting effect of aminophytol.
Figure 3:
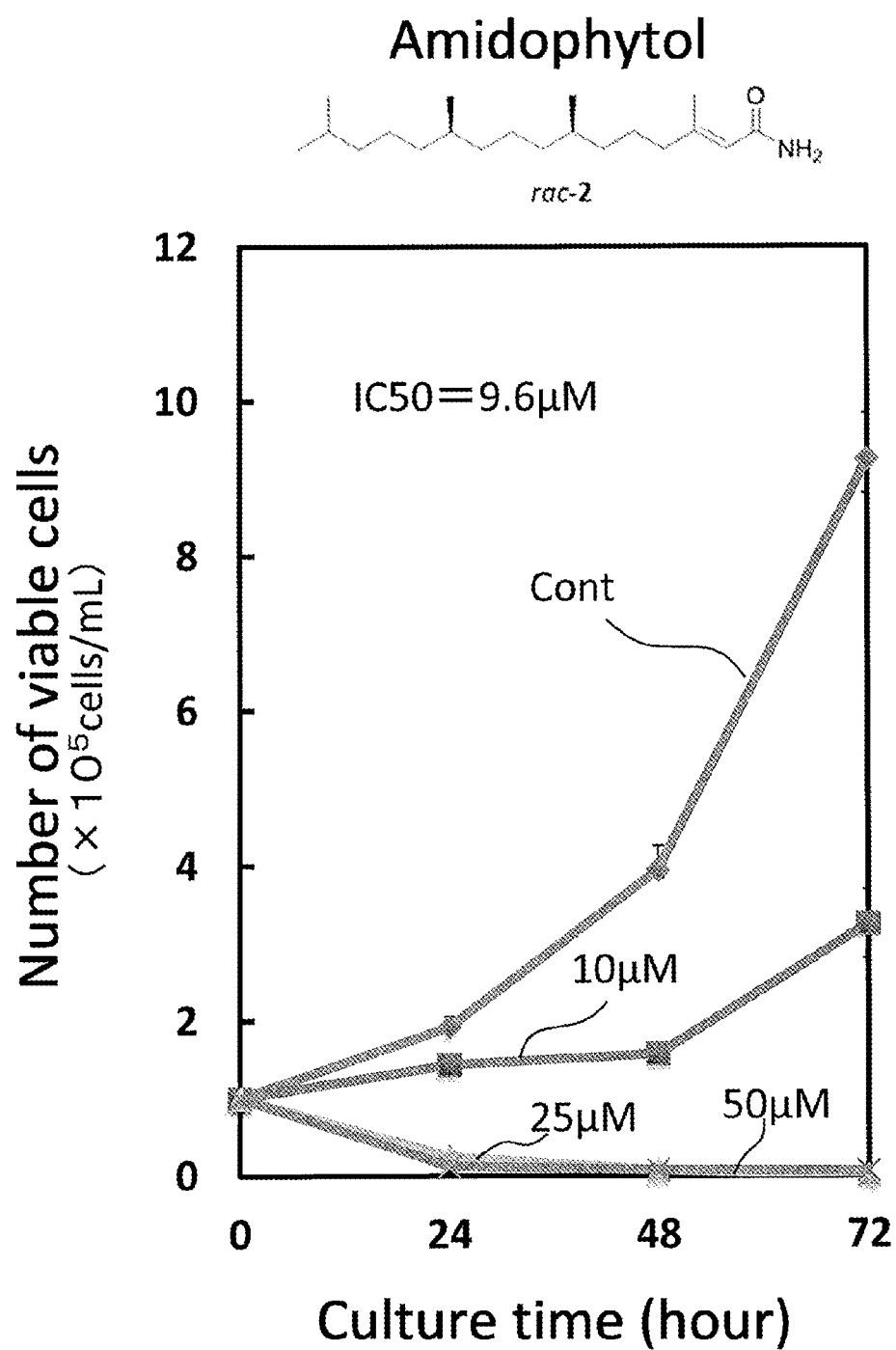
FIG. 3 is a graph showing cancer cell growth inhibiting effect of amidophytol.
Figure 4:
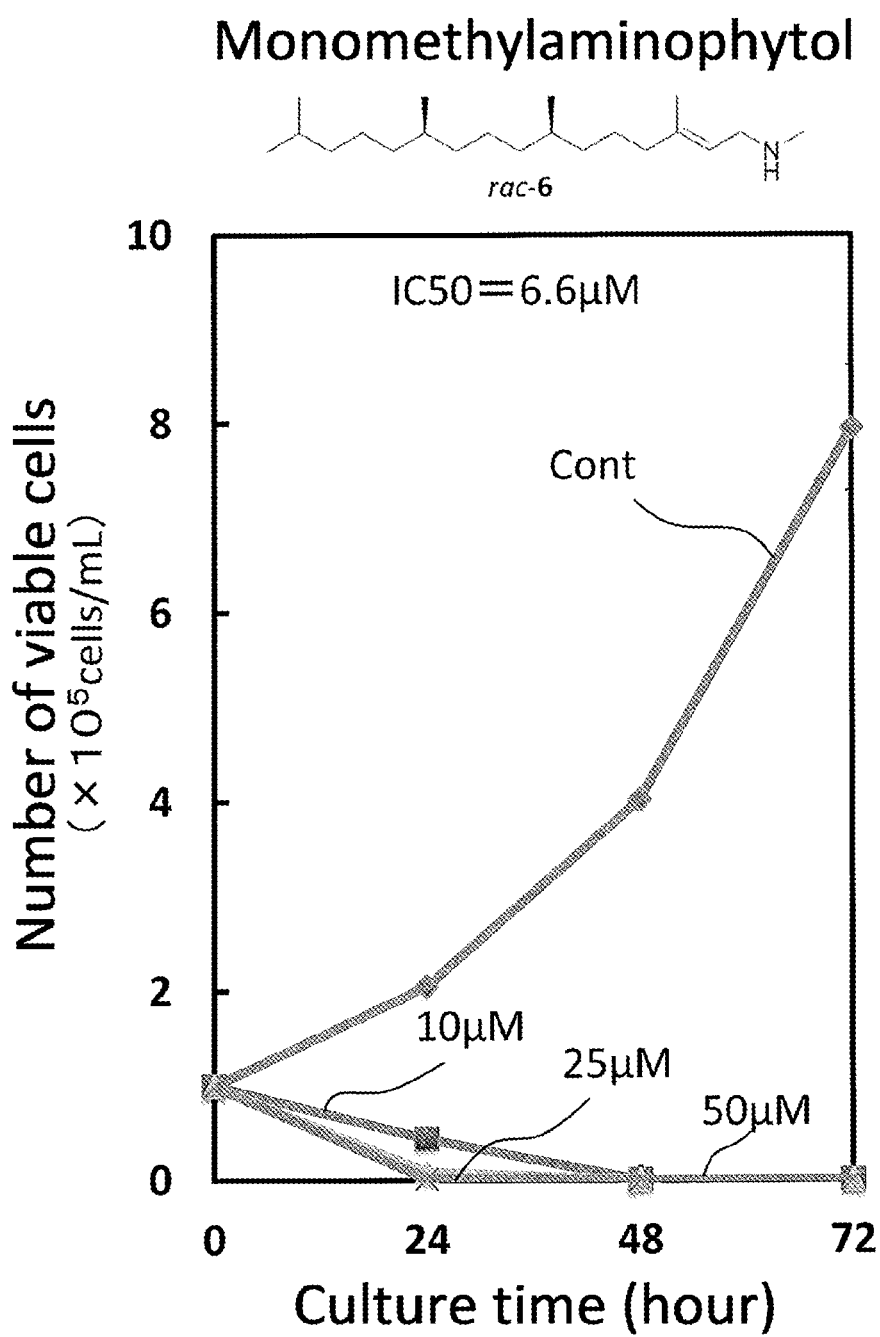
FIG. 4 is a graph showing cancer cell growth inhibiting effect of (mono) methylaminophytol.
Figure 5:
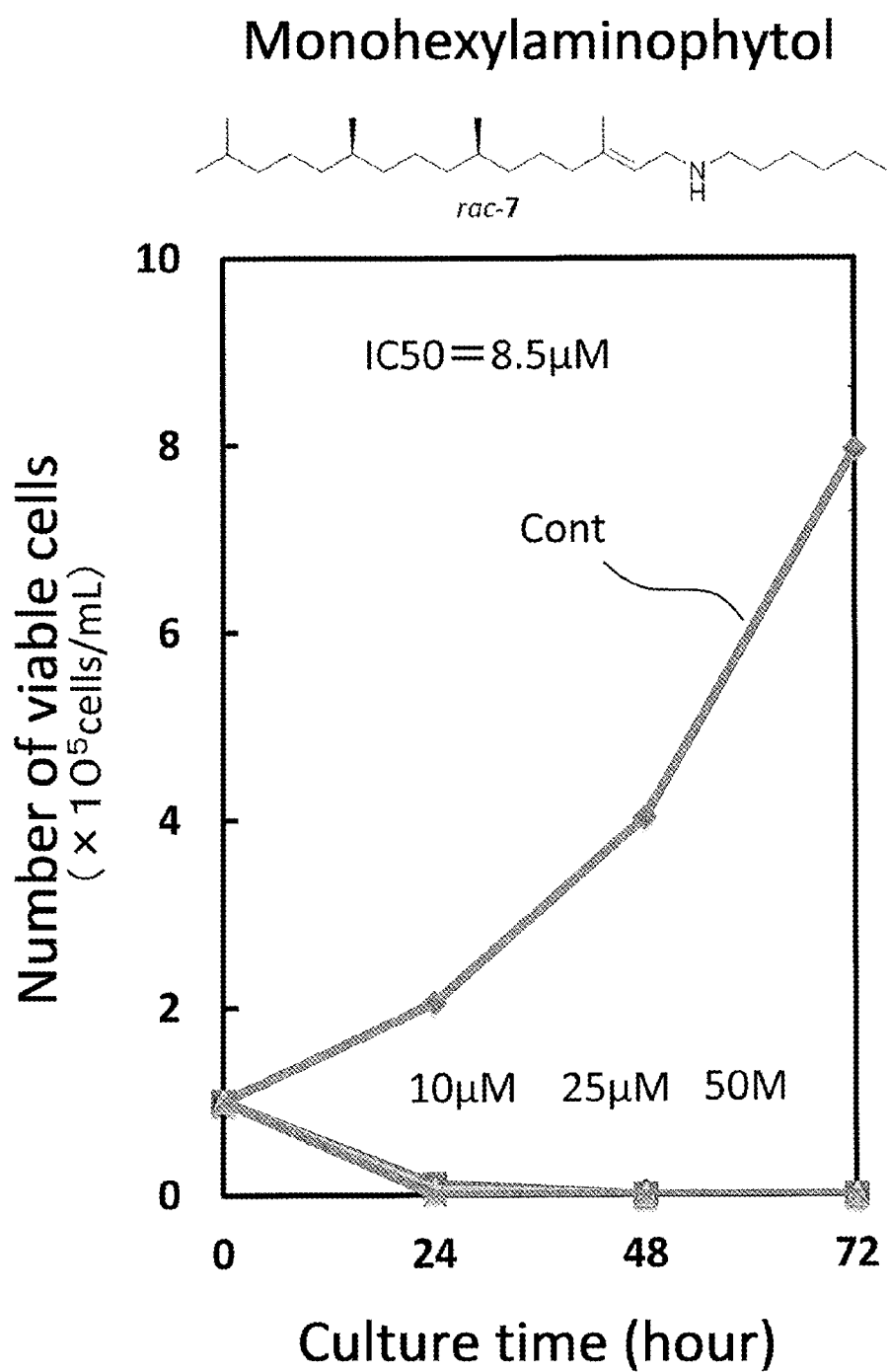
FIG. 5 is a graph showing cancer cell growth inhibiting effect of (mono) hexylaminophytol.
Figure 6:
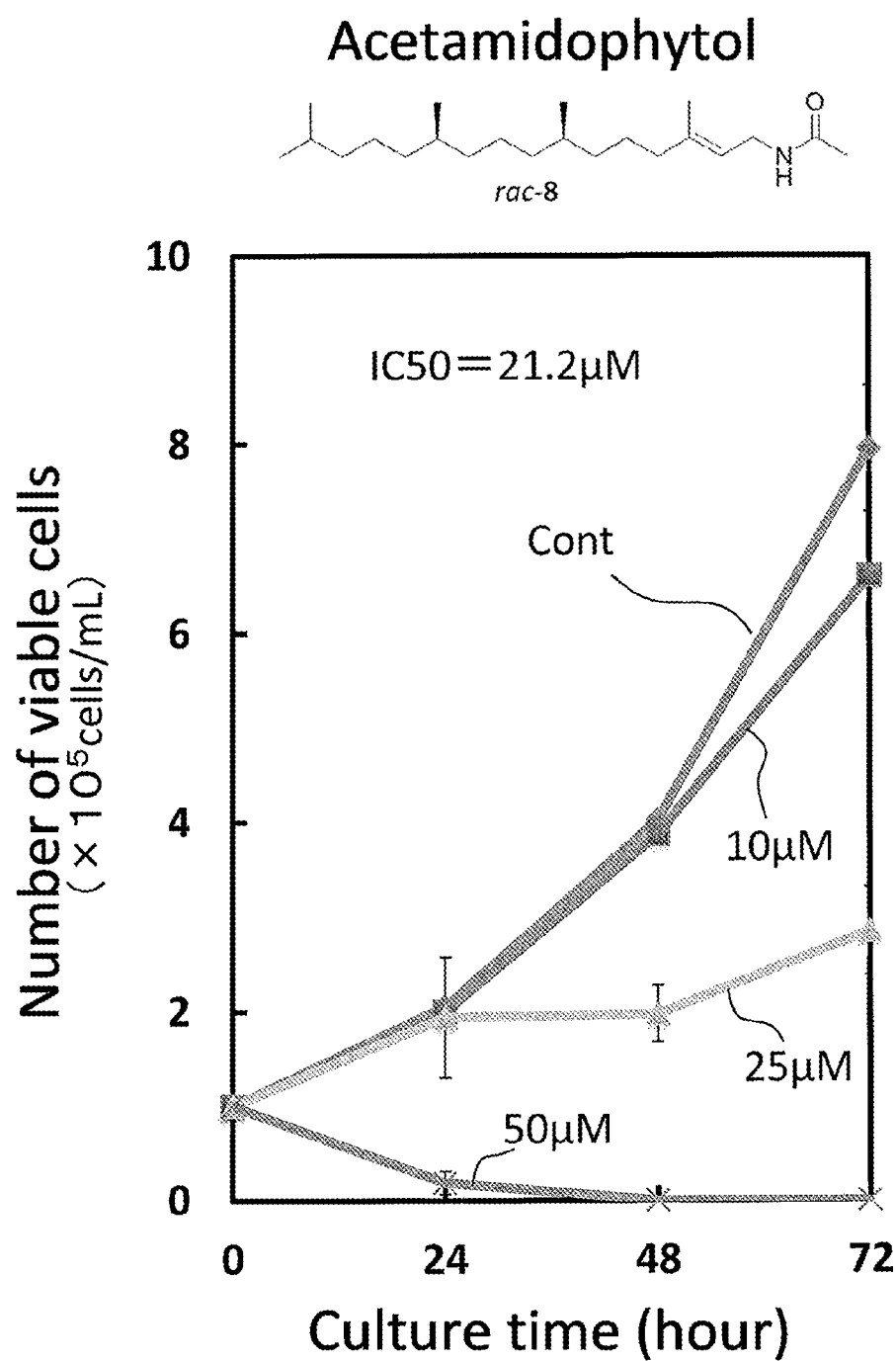
FIG. 6 is a graph showing cancer cell growth inhibiting effect of acetamidophytol.

Results are shown in FIG. 1 to FIG. 6. A horizontal axis represents culture time (hours) and a vertical axis represents the number of viable cells (×10$^5$ cells/mL). "Cont" in the figures represents the control, and "10 μM," "25 μM," and "50 μM" represent concentration. FIG. 1 is for phytol; FIG. 2 is for aminophytol; FIG. 3 is for amidophytol; FIG. 4 is for monomethylaminophytol; FIG. 5 is for monohexylaminophytol; and FIG. 6 is for acetamidophytol. Phytol inhibited the growth of Jurkat cells (cancerous cells) as shown in Patent Literature 1 and concentration-dependence was also observed.

In contrast, aminophytol, amidophytol, monomethylaminophytol and monohexylaminophytol, and acetamidophytol exhibited more effect than phytol. More specifically, with phytol, viable cells could still be identified after 72 hours at a concentration of 50 μM, whereas with aminophytol, amidophytol, monomethylaminophytol, and monohexylaminophytol, few cells survived after 24 hours at a concentration of 25 μM. With acetamidophytol, viable cells could still be identified even at a concentration of 25 μM, whereas few cells survived at a concentration of 50 μM.

Results of IC50 for respective compounds are shown in graphs. It was found that IC50 for phytol was 29.8 μM, whereas IC 50 was 3.8 μM for aminophytol, 9.6 μM for amidophytol, 6.6 μM for monomethylaminophytol, and 8.5 μM for monohexylaminophytol, and that they were more than an order of magnitude more effective than phytol. Acetamidophytol was 21.2 μM, which was lower than that of phytol.

INDUSTRIAL APPLICABILITY

The cancer cell growth inhibiting composition according to the present invention can be suitably utilized for the treatment and prevention of cancers.

The invention claimed is:

1. A cancer cell growth inhibiting composition comprising at least one of compounds having a structure represented by Formula (1), Formula (2), Formula (6), Formula (7) or Formula (8), or a pharmaceutically acceptable salt thereof as main components:

[Chemical 100]

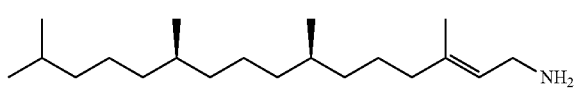

(1)

[Chemical 101]

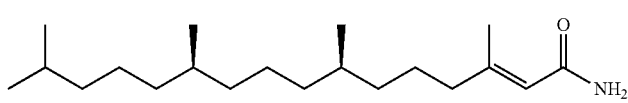

(2)

[Chemical 102]

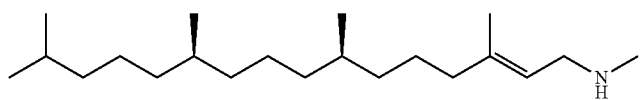

(6)

[Chemical 103]

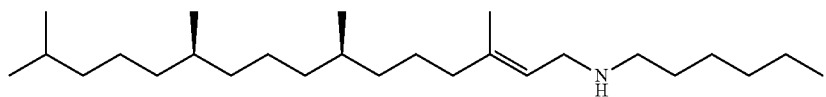

(7)

[Chemical 104]

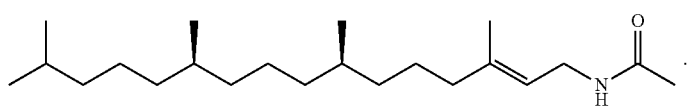

(8)

2. A processed food comprising a compound having a structure represented by Formula (8), or a pharmaceutically acceptable salt thereof:

[Chemical 109]

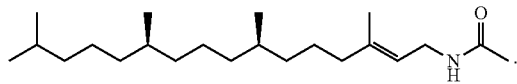

(8)

3. A compound having the structure of formula (8):

[Chemical 113]

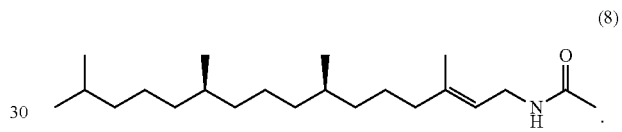

(8)

4. An anti-cancer pharmaceutical composition comprising the cancer cell growth inhibiting composition according to claim 1.

5. An oral dosage form comprising the anti-cancer pharmaceutical composition of claim 4.

6. A method of treating leukemia comprising administering the anti-cancer pharmaceutical composition according to claim 4 to a patient with leukemia.

7. The method of claim 6 wherein the pharmaceutical composition is an oral dosage form.

8. The processed food according to claim 2, wherein the processed food is a nutritional function food.

\* \* \* \* \*